US00PP14275P39

(12) United States Plant Patent
Meilland

(10) Patent No.: US PP14,275 P3
(45) Date of Patent: Nov. 4, 2003

(54) HYBRID TEA ROSE PLANT NAMED 'MEIWILING'

(50) Latin Name: *Rosa hybrida*
Varietal Denomination: Meiwiling

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 10/319,543

(22) Filed: Dec. 16, 2002

(65) Prior Publication Data

US 2003/0140385 P1 Jul. 24, 2003

(51) Int. Cl.[7] ..... A01H 5/00

(52) U.S. Cl. ..... Plt./137

(58) Field of Search ..... Plt./130, 137

*Primary Examiner*—Bruce R. Campell
*Assistant Examiner*—Annette H. Para
(74) *Attorney, Agent, or Firm*—Burns, Doane, Swecker & Mathis, L.L.P.

(57) ABSTRACT

A new and distinct variety of Hybrid Tea rose plant is provided which forms attractive double blossoms that are mauve in coloration. The buds are large and high-pointed. The plant exhibits a narrow bushy growth habit, rather dense semi-glossy foliage, and very good tolerance to Powdery Mildew and Botrytis. The foliage coloration contrasts nicely with the mauve blossom coloration. The new variety is particularly well suited for cut flower production under greenhouse growing conditions.

1 Drawing Sheet

Figures 1, 2, 3, 4, 5, 6, 7, 8, 9, 10, 11, 12, 13, 14, 15:
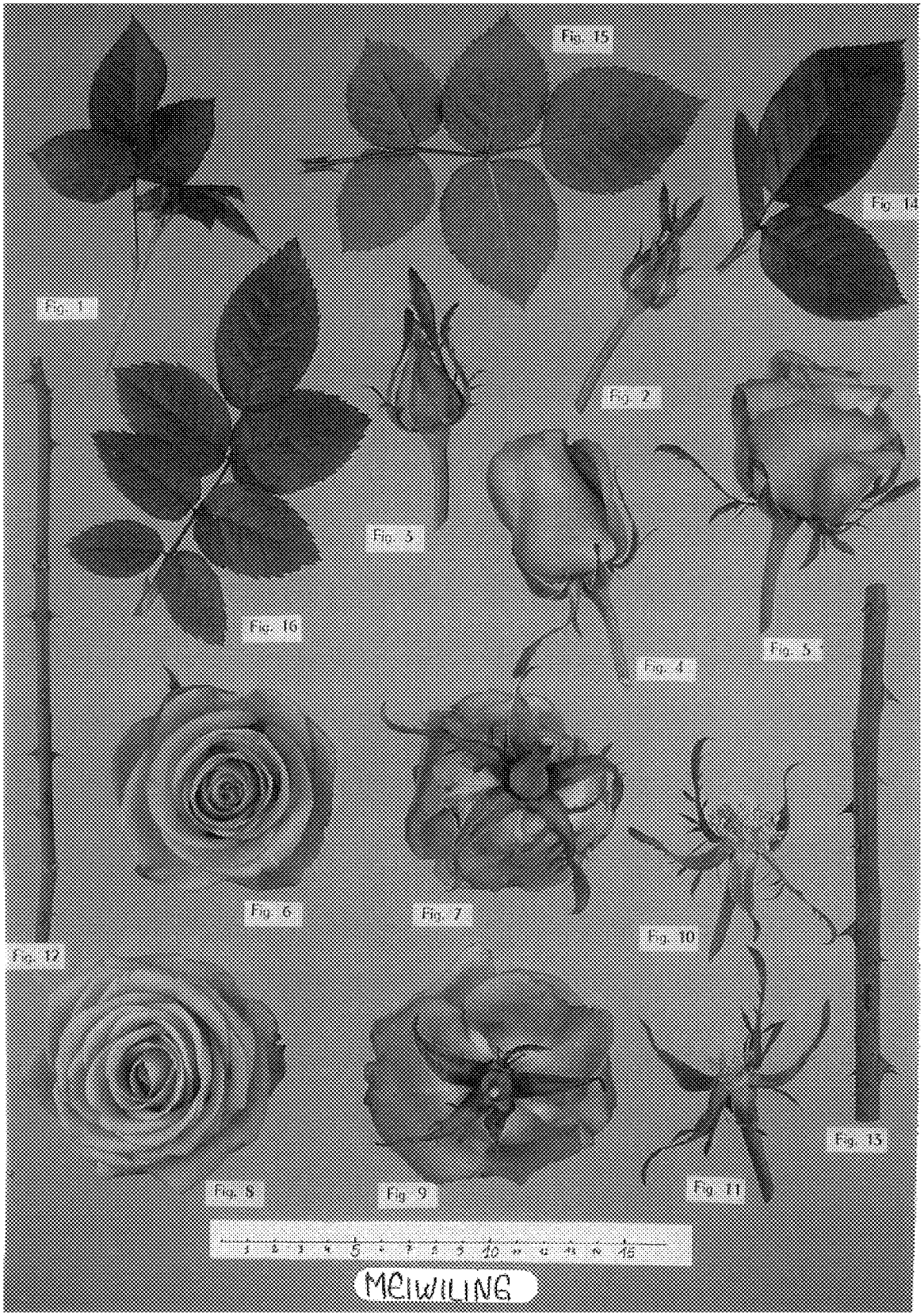

Botanical/commercial classification: *Rosa hybrida*/Hybrid Tea Rose Plant.
Varietal denomination: cv. 'Meiwiling'.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'Sterling Silver' variety (U.S. Plant Pat. No. 1,433) and the 'Mme. A. Meilland' variety (U.S. Plant Pat. No. 591). The 'Mme. A. Meilland' variety sometimes is known as the 'Peace' variety. The male parent (i.e., the pollen parent) was the 'Meigormon' variety (U.S. Plant Pat. No. 8,647). The parentage of the new variety can be summarized as follows:

('Sterling Silver'×'Mme. A. Meilland')×'Meigormon'.

The seeds resulting from the above pollination were sown and small plants were obtained which were physically and biologically different from each other. Selective study resulted in the identification of a single plant of the new variety.

It was found that the new Hybrid Tea variety of the present invention (a) exhibits a narrow bushy growth habit, (b) forms attractive large high-pointed buds, (c) forms on a nearly continuous basis attractive double mauve-colored blossoms, (d) forms semi-glossy foliage that contrasts well with the mauve blossom coloration, and (e) is particularly well suited for cut flower production under greenhouse growing conditions.

The disease tolerance is very good with respect to Powdery Mildew and Botrytis.

The new variety well meets the needs of the horticultural industry and can be used for the commercial production of cut flowers when grown indoors.

The new variety can be readily distinguished from its ancestors. For instance, the 'Sterling Silver' variety forms lighter colored blossoms that display an intense fragrance and forms darker more glossy foliage. The 'Mme. A. Meilland' variety forms golden yellow blossoms having rose-pink edges and a slight fragrance. The 'Meigormon' variety forms smaller buds and red blossoms.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meiwiling' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during February while budded on *Rosa indica* understock and growing in greenhouses at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of two year-old plants during February while budded on *Rosa indica* understock and growing in greenhouses at Le Cannet des Maures, Var, France.

Class: Hybrid Tea.

Plant:

*Height.*—Approximately 150 cm when the petals start to open.

*Width.*—Approximately 50 to 60 cm.

*Habit.*—Narrow and bushy.

Branches:

*Color.*—Young stems: medium green, near Yellow-Green Group 146B and 146C. Adult wood: medium green, near Yellow-Green Group 147B.

*Thorns.*—Size: variable (as illustrated). Quantity: on 20 mm of adult stems approximately 15 on average that are approximately 0.8 cm in length. Color: near Greyed-Red Group 182D on adult wood. Configuration: elongated and slightly curved downwards on the upper surface and concave under surface.

Leaves:

*Stipules.*—Adnate, pectinate, and broad, approximately 1.5 cm in length on average and approximately 0.5 cm in width on average.

*Petioles.*—Upper surface: rather glandular, and near Yellow-Green Group 147A lightly suffused with Greyed-Red Group 182A in coloration. Under surface: bears small prickles, and near Greyed-Green Group 191B in coloration. Length: approximately 2 cm with the terminal leaflet.

*Leaflets.*—Number: 3, 5 (most often), and 7. Shape: elliptic to ovate (as illustrated) with a rounded base and a somewhat cuspidate generally symmetrical tip (as illustrated). Size: the terminal leaflets commonly are approximately 6.5 cm in length and approximately 3.5 cm in width on average. Serration: small and single (as illustrated). Texture: thick. General appearance: rather dense with a semi-glossy aspect. Color (young foliage): Upper surface: near Yellow-Green Group 147A and lightly suffused at the edge with Greyed-Red Group 182A. Under surface: near Yellow-Green Group 147B and suffused with Greyed-Red Group 182A. Color (adult foliage): Upper surface: Green Group 139A. Under surface: near Greyed-Green Group 191B.

Inflorescence:

*Number of flowers.*—Commonly one per stem.

*Peduncle.*—Commonly approximately 7 cm in length, possesses a glabrous surface, and near Yellow-Green Group 146B in coloration.

*Sepals.*—Upper surface: tomentose and near Greyed-Green Group 191A in coloration. Under surface: smooth and near Yellow-Green 147A in coloration. Configuration: elongated, three sepals commonly possess extensions (as illustrated), and two sepals commonly possess no extensions.

*Buds.*—Shape: conical. Size: large (as illustrated). Length: approximately 5 cm on average. Color: Upper surface: near Purple Group 75B and lightly suffused with Purple Group 75A. Under surface: near Purple Group 75B and suffused with Purple Group 75A.

*Flower.*—Shape: high-pointed. Diameter: approximately 10 cm on average. Color (when blooming): Upper surface: near Purple Group 75B and lightly suffused with Purple Group 75A. Under surface: near Purple Group 75B and lightly suffused with Purple Group 75A. Basal petal spot: none present. Fragrance: none. Lasting quality: very long with the blossoms commonly lasting approximately 20 days on the plant on average, and approximately 14 days when cut and placed in a vase on average. Petal number: approximately 40 on average under normal growing conditions. Petal shape: rounded base, and commonly reflexed and undulated at the edges. Petal texture: relatively thick. Petal arrangement: imbricated. Petal drop: moderately good. Stamen number: approximately 90 on average. Anthers: regularly arranged around the styles, approximately 0.3 cm in size, and near Yellow-Orange Group 22B in coloration. Pollen: present and near Yellow-Orange Group 15A in coloration. Filaments: approximately 0.7 cm in length and near Yellow Group 5D in coloration. Pistils: approximately 80 on average. Stigmas: approximately 0.1 cm in size, and near Yellow Group 11B in coloration. Styles: approximately 0.9 cm in length on average and near Yellow Group 10C in coloration. Receptacle: approximately 0.7 cm in length on average, approximately 0.8 cm in width on average, smooth, near Yellow-Green Group 146B in coloration, and funnel-shaped in longitudinal section. Hips: the plant has been grown under greenhouse growing conditions to date commonly with the cutting of blossoms. Accordingly, no hips have been observed.

Devlopment:

*Vegetation.*—Medium.

*Blooming.*—Normally abundant and nearly continuous.

*Tolerance to diseases.*—Very good with respect to Powdery Mildew and Botrytis.

*Aptitude to forcing.*—Very good.

I claim:

1. A new and distinct variety of Hybrid Tea rose plant characterized by the following combination of characteristics:

(a) exhibits a narrow bushy growth habit, (b) forms attractive large high-pointed buds, (c) forms on a nearly continuous basis attractive double mauve-colored blossoms, (d) forms semi-glossy foliage that contrasts well with the mauve blossom coloration, and (e) is particularly well suited for cut flower production under greenhouse growing conditions.

substantially as herein shown and described.

* * * * *

MEIWILING